(12) United States Patent
de Voir et al.

(10) Patent No.: US 10,292,599 B2
(45) Date of Patent: May 21, 2019

(54) IMPLANTABLE CARDIAC DEVICE ADAPTED TO EXTRACT A PATIENT'S RESPIRATORY WAVEFORMS FROM AN INTRATHORACIC OR INTRACARDIAC IMPEDANCE, PRESSURE AND/OR ACCELEROMETRY INPUT STREAM

(71) Applicant: BIOTRONIK SE & Co. KG, Berlin (DE)

(72) Inventors: Christopher S. de Voir, Tigard, OR (US); J. Christopher Moulder, Portland, OR (US); Jie Lian, Beaverton, OR (US); Dirk Muessig, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 947 days.

(21) Appl. No.: 14/249,580

(22) Filed: Apr. 10, 2014

(65) Prior Publication Data
US 2014/0309539 A1 Oct. 16, 2014

Related U.S. Application Data

(60) Provisional application No. 61/812,264, filed on Apr. 16, 2013.

(51) Int. Cl.
*A61B 5/0205* (2006.01)
*A61B 5/042* (2006.01)
(Continued)

(52) U.S. Cl.
CPC .......... *A61B 5/0205* (2013.01); *A61B 5/0215* (2013.01); *A61B 5/042* (2013.01);
(Continued)

(58) Field of Classification Search
CPC .......... A61B 5/053; A61B 5/72; A61B 5/726; A61B 5/08; A61B 5/0809; A61B 5/7203; A61B 5/7235
See application file for complete search history.

(56) References Cited

U.S. PATENT DOCUMENTS 6,757,343 B1 6/2004 Ortega et al.
7,988,634 B1 8/2011 Koh
(Continued)

FOREIGN PATENT DOCUMENTS

CA 2428393 11/2004
EP 1 769 737 4/2007
(Continued)

OTHER PUBLICATIONS

European Search Report and Annex to the European Search Report on European Patent Application No. EP 14 16 3708, dated Aug. 4, 2014 (10 pages).
(Continued)

*Primary Examiner* — Puya Agahi
(74) *Attorney, Agent, or Firm* — Buchanan Ingersoll & Rooney PC

(57) ABSTRACT

An implantable cardiac device is provided. The implantable cardiac device includes a sensing unit adapted to measure an intrathoracic or intracardiac impedance, pressure, and/or accelerometry input stream, which includes a patient's respiratory waveforms. Furthermore, the implantable cardiac device includes a quantizer-unit adapted to sample the input stream with an initial sampling frequency Fs, providing input samples of the input stream. The implantable cardiac device further includes a filter bank 50 suited to perform a streaming Wavelet transformation on the input samples on a sample-by-sample basis, using the initial sampling frequency Fs provided by the quantizer-unit, wherein the streaming Wavelet transformation is adapted to perform a (Continued)

source separation, extracting, and separating the respiratory waveforms of the input stream.

13 Claims, 8 Drawing Sheets

(51) Int. Cl.
| | |
|---|---|
| *A61B 5/04* | (2006.01) |
| *A61B 5/00* | (2006.01) |
| *A61B 5/0215* | (2006.01) |
| *A61B 5/11* | (2006.01) |
| *A61B 5/08* | (2006.01) |
| *A61B 5/053* | (2006.01) |

(52) U.S. Cl.
CPC ........ *A61B 5/04017* (2013.01); *A61B 5/0816* (2013.01); *A61B 5/1102* (2013.01); *A61B 5/686* (2013.01); *A61B 5/726* (2013.01); *A61B 5/053* (2013.01); *A61B 5/72* (2013.01); *A61B 5/7203* (2013.01); *A61B 5/7235* (2013.01)

(56) References Cited

U.S. PATENT DOCUMENTS

| | | | |
|---|---|---|---|
| 8,065,005 | B1 | 11/2011 | Wong et al. |
| 2004/0260188 | A1* | 12/2004 | Syed .................. A61B 5/0456 600/509 |
| 2005/0240087 | A1* | 10/2005 | Keenan ................ A61B 5/0205 600/301 |
| 2008/0109041 | A1 | 5/2008 | de Voir |
| 2009/0048497 | A1* | 2/2009 | Keren ................ A61B 5/02028 600/301 |
| 2010/0305647 | A1* | 12/2010 | McCabe ............ A61B 5/04001 607/18 |
| 2011/0082484 | A1* | 4/2011 | Saravia ................ A61B 5/0031 606/167 |
| 2011/0213271 | A1* | 9/2011 | Telfort ................... A61B 7/003 600/586 |
| 2013/0030486 | A1 | 1/2013 | Betzold |
| 2013/0079657 | A1 | 3/2013 | Ochs et al. |

FOREIGN PATENT DOCUMENTS

| | | |
|---|---|---|
| WO | 02097718 | 12/2002 |
| WO | 2010033400 | 3/2010 |
| WO | 2013043157 | 3/2013 |

OTHER PUBLICATIONS

Hall, Peter et al., "Wavelet-Based Estimation with Multiple Sampling Rates", The Annals of Statistics (vol. 32, No. 5, Oct. 1, 2004) pp. 1933-1956.

Yi, W.J. et al., "Derivation of Respiration from ECG Measured Without Subject's Awareness Using Wavelet Transform", Second Joint EMBS/BMES Conference 2002; 24th Annual International Conference of the Engineering in Medicine and Biology Society, Oct. 23-26, 2002 (Ann. vol. 1, Oct. 23, 2002) pp. 130-131.

Daubechies, I. et al., "Factoring Wavelet Transforms Into Lifting Steps", The Journal of Fourier Analysis and Applications, CRC Press, Boca Raton, Florida, US (vol. 4, No. 3, Dec. 31, 1998) pp. 247-269.

European Office Action dated Nov. 10, 2017, of the corresponding European Patent Application No. 14 163 708.2 (7 pages).

Xin Zhu et al., "Real-Time Monitoring of Respiration Rhythm and Pulse Rate During Sleep", IEEE Transactions on Biomedical Engineering, vol. 53, No. 12, Dec. 1, 2006, pp. 2553-2563.

* cited by examiner

IMPLANTABLE CARDIAC DEVICE ADAPTED TO EXTRACT A PATIENT'S RESPIRATORY WAVEFORMS FROM AN INTRATHORACIC OR INTRACARDIAC IMPEDANCE, PRESSURE AND/OR ACCELEROMETRY INPUT STREAM

CROSS-REFERENCE TO RELATED APPLICATIONS

This patent application claims the benefit of U.S. Provisional Patent Application No. 61/812,264, filed on Apr. 16, 2013, the disclosure of which is hereby incorporated by reference in its entirety.

FIELD OF THE INVENTION

The present invention generally relates to an implantable cardiac device that is adapted to measure an intrathoracic or intracardiac impedance, pressure, and/or accelerometry input stream which comprises a patient's respiratory waveforms, wherein the implantable cardiac device is suited to perform a streaming Wavelet transformation on the input stream to perform a source separation, extracting, and separating the respiratory waveforms from the input stream.

STATE OF ART

Accurate real time detection of a patient's respiratory waveforms has been an important concern in the field of cardiology in the recent years. Of the known solutions in the state of the art that address the subject of respiration detection, only a few have appeared in implantable cardiac devices. Most of those solutions realizable within an implantable cardiac device, for example, those that derive the respiration from an R-wave amplitude, are exposed to various sources of error, as for example aliasing due to an undersampling. Furthermore, most of the solutions known in the state of art are based on conventional digital filtering which distorts the physiological waveform or does not adapt to the non-stationary character of respiration and the out-of-band information which confounds its fidelity. Moreover, in some solutions of the prior art, multiple designs are implemented within an implantable cardiac device to adapt to continuously changing circumstances of in- and out-band waveform components, at the cost of an high energy consumption and a complicated circuit design or a large memory space.

For example, U.S. Pat. No. 8,065,005 discloses an implantable cardiac device that comprises a pulse generator which is configured to produce pulses that are applied to the bodily tissue, wherein the pulses are used to measure a physiological parameter, wherein each pulse has a multiphasic waveform consisting of positive and negative phases. Furthermore, each phase comprises a duration and an amplitude, wherein duration is defined as the width of the phase and the amplitude is defined as the length of the phase. Moreover, the implantable cardiac device disclosed in U.S. Pat. No. 8,065,005 comprises a circuit in the pulse generator to vary the duration of the pulses and a signal processor to detect a change in the shape of the sensed response waveforms resulting from application of the pulses of various durations.

Another cardiac device adapted for implant in a patient is disclosed in the U.S. Pat. No. 7,988,634, wherein the cardiac device disclosed therein comprises sense circuits which are adapted to obtain a composite signal which contains a cardiac component and a respiratory component. The cardiac device disclosed in U.S. Pat. No. 7,988,634 further comprises a respiratory signal canceller which comprises an adder adapted to subtract the respiratory signal from the composite signal to reduce the respiratory component of the composite signal, and an adaptive filter adapted to adaptively filter the respiratory signal. The adaptive filter required in this solution suffers from adaptation latency. Adaptive filters are based on assumptions of stationarity during the adaptation step. Because stationarity is not a reliable property of real physiological waveforms, the filtering performed by the cardiac device of U.S. Pat. No. 7,988,634 risks non-convergence during the adaptation step.

While the use of the Wavelet transform in the field of cardiology is well known in the prior art, even for the extraction of physiological signals of a signal input stream, it is used for de-noising and compression and does not appear as a tool for source separation of respiration. Moreover, its implementation in an implantable cardiac device is often very costly.

The present invention is directed toward overcoming one or more of the above-identified problems.

DISCLOSURE OF THE INVENTION

According to the present invention, an implantable cardiac device is provided. The implantable cardiac device comprises a sensing unit adapted to measure a physiological signal like an intrathoracic or intracardiac impedance, pressure, or accelerometry signal input stream, which comprises a patient's respiratory waveforms. Furthermore, the implantable cardiac device comprises a quantizer-unit adapted to sample the input stream with an initial sampling frequency Fs, providing input samples of the input stream. The implantable cardiac device further comprises a filter bank suited to perform a streaming Wavelet transformation on the input samples on a sample-by-sample basis, using the initial sampling frequency Fs provided by the quantizer-unit, wherein the streaming Wavelet transformation is adapted to perform a source separation, extracting, and separating the respiratory waveforms of the input stream.

The advantage of such an implantable cardiac device is that it directly accepts input streams containing the respiration of a patient and produces output in real time without the necessity for matrix processing. Furthermore, through the use of a Wavelet transformation in the sense as described above, it is possible to separately extract cardiac motion and respiration components from the input stream in order to preserve the same for subsequent analysis either as isolated signals or in interaction with each other. This is in contrast to the conventional use the Wavelet transformation. Expressed in other words, the use of an implantable cardiac device according to the present invention enables an accurate and reliable generation of a patient's respiration waveform and to measure the fiducial points of a patient's breath cycle and to accurately preserve the relative time location of those fiducial points with respect to the fiducial points of other physiologic signals, that is, minimize group delay and maintain concurrency of fiducial points.

In a preferred embodiment, the initial sampling frequency Fs of the quantizer-unit is adaptable. Through the adaptable initial sampling frequency Fs, the operation of the implantable cardiac device can be adapted to advantageously meet the requirements for respiration detection for various types of disease patterns affecting the respiration rate of a patient as, for example, Apnea or Tachypnea. Through an adjustment of the initial sampling frequency Fs and according to that, an adjustment of the sampling frequencies or the sample rates used throughout the performance of the Wavelet transformation, the Nyquist frequency can arbitrarily be placed within the frequency band that is evaluated. It is especially preferred to place at least one boundary frequency between the fundamental of cardiac dynamics and the upper passband edge of respiration. Furthermore, through an adjustment of the initial sampling frequency Fs, a selection of frequency sub-bands that are given within the input samples is performable, whereas the filter bank or its coefficients need not to be concomitantly changed. In a conventional digital filter, a change in a sample rate or the initial sampling frequency Fs requires a change to new filter bank coefficients designed for the new sample rate that must be stored or loaded into the respective implantable cardiac device, which is not the case in the present invention.

Preferably, the initial sampling frequency Fs of the quantizer-unit is adapted according to a change in the heart rate and/or a change in the breathing rate of a patient. In such an embodiment, the implantable cardiac device is especially capable of detecting different respiration health states. Furthermore, with such an embodiment, an adaptation of the initial sampling frequency Fs is performable when needed, in order to improve the discrimination of a physiological signal from an input stream.

In a preferred embodiment, the Wavelet transformation performed by the filter bank is a Haar Lifting Wavelet Transformation. Such a Wavelet transformation is especially suitable for the purpose mentioned herein because, among others, its implementation within the filter bank of an implantable cardiac device has a relatively low implementation cost.

In another preferred embodiment, the filter bank is realized within a digital signal processing unit. Preferably, the Wavelet transformation is realized by means of a recursive algorithm. In an even more preferred embodiment, the filter bank is realized by means of a recursive algorithm that maximizes the code reuse. Through such a realization of the filter bank, the initial sampling frequency Fs can be changed or adapted easily to allow a maximal discrimination of a physiological signal, without that a concomitant change to the filter bank is needed in order to keep it working properly. Furthermore, through such an implementation, memory space and processing capacity can be saved. Preferably, the Wavelet transformation is realized within a digital signal processing unit.

In a preferred embodiment, the filter bank is adapted to perform a streaming Wavelet transformation comprising a forward transformation and a backward transformation, wherein during the forward transformation, the Wavelet transformation is applicable on each input sample provided by the quantizer-unit generating output data on "n" different sampling levels, wherein the output data generated on the sampling levels is queued and the sampling frequency used to sample an input sample on a sampling level "t" is equal to 2 times the sampling frequency of the sampling level t−1, wherein "n" and "t" are elements of $N^+$. Expressed in other words, the filter bank is adapted to perform operations on each input sample, wherein the output data of the Wavelet transformation is retained in a central queue structure where the length of the queue is equal to $2(n-t)-1$. The purpose of such a queuing structure is to maintain concurrency between the frequency sub-bands given within the input samples evaluated. In a further preferred embodiment, the Wavelet transformation provides for zero wait ($2^0-1=0$) at its lowest level, which results in a shortening of the length of all queues.

Preferably, the output data of a sampling level "t" that is not needed for a reconstruction of a respiratory waveform is discardable and excludable from the queuing process during the performance of the Wavelet transformation, after it has been used for the calculation of the output data of the sample level t−1. Expressed in other words, output data of the forward transformation representing frequency sub-bands of an input sample, which is not needed for the reconstruction of a respiratory waveform within the performance of the Wavelet transformation, can be discarded after it has been used to compute or generate output data of a lower frequency sub-band, in order to decrease memory usage, energy consumption and processing activity.

In a preferred embodiment, the information, whether output data is needed for the reconstruction of a respiratory waveform, or discarded from the Wavelet transformation, is stored as a Boolean value in an indication vector. In a further preferred embodiment, the indication vector also serves to gate the input on the reconstruction side or the backwards transformation of the Wavelet transformation.

In a preferred embodiment, during the backwards transformation, an upsampling is also only performable up to the highest sampling level on which output data is retained, wherein the output data of the input samples transformed on that highest sampling level is evaluable with the sampling frequency of that highest sampling level. In such an embodiment, an upsampling is also only performable up to those sampling levels on which output data is existing, capturing only the information of the frequency sub-bands relevant and excluding those frequency sub-bands irrelevant from the Wavelet transformation. So an upsampling does not have to be performed back up to the initial sampling frequency Fs of the forward transformation, whereby memory usage, energy consumption and processing activity is reduced though fiducial concurrency with other signals, and if applicable, is preserved.

Preferably, during the backward transformation, an upsampling of the output data generated during the forward transformation is performable beyond the sampling level of the initial sampling frequency Fs used within the forward transformation and evaluable on that sampling level. In such an embodiment, the output data of two different transformed input samples can be evaluated together, since the output data of an input sample that was sampled with a low sample rate can be upsampled to a higher sample rate, a second input sample of the same or a different input stream was sampled with.

In a preferred embodiment, within the backward transformation, the output data of at least two different transformed input samples of the same input stream can be upsampled to the same sampling frequency and be evaluated simultaneously with the sampling frequency they have been upsampled to. Expressed in other words, two or more distinct physiological signals can be simultaneously extracted from different frequency sub-bands of the same input stream while maintaining their concurrency. Furthermore, the two or more distinct physiological signals can be evaluated with the same sampling frequency. So within the backward transformation, the output data that has been transformed in at least two different ways from a single input stream can be upsampled to the same sampling frequency and be evaluated simultaneously with the sampling frequency they have been upsampled to.

Preferably, a parameter and/or a probabilistic function is computable for at least one input sample, wherein the parameter or the probabilistic function provides information about at least one of a predefined characteristic of that input sample, statistical distribution of that input sample and a statistical distribution related to that input sample. In such an embodiment of the present invention, various properties of an input sample or its frequency sub-bands can be computed, which, for example, can be related to the respiration rate of a patient.

In a preferred embodiment, the computed parameter and/or the computed probabilistic function is storable in a vector. Such a vector can function both as an information source, for example, providing information about the instantaneous and/or sample-wide cross section of a decomposed input sample, and as a control point for the indication vector mentioned above, wherein the kind of the Boolean value stored in a slot of the indication vector depends on the appendant computed parameter and/or the computed probabilistic function stored in the vector.

Preferably, the parameter represents the average energy of a respective input sample or the scale value used during the Wavelet transformation of a respective input sample. In such an embodiment, each frequency sub-band of the input sample of an input stream is properly quantifiable in its dimension.

In the context mentioned above, the Nyquist frequency is the frequency limit Fs/2 and corresponds to the upper passband edge of the topmost frequency sub-band, assuming that the Wavelet transform receives input directly from the quantizer-unit and is sampling at the initial sampling frequency Fs, and assuming that the input stream or input signal is adequately antialias filtered prior to the sampling and/or sampled at an adequate sampling rate to prevent aliasing.

Further features, aspects, objects, advantages, and possible applications of the present invention will become apparent from a study of the exemplary embodiments and examples described below, in combination with the Figures, and the appended claims.

DETAILED DESCRIPTION

Figure 1:
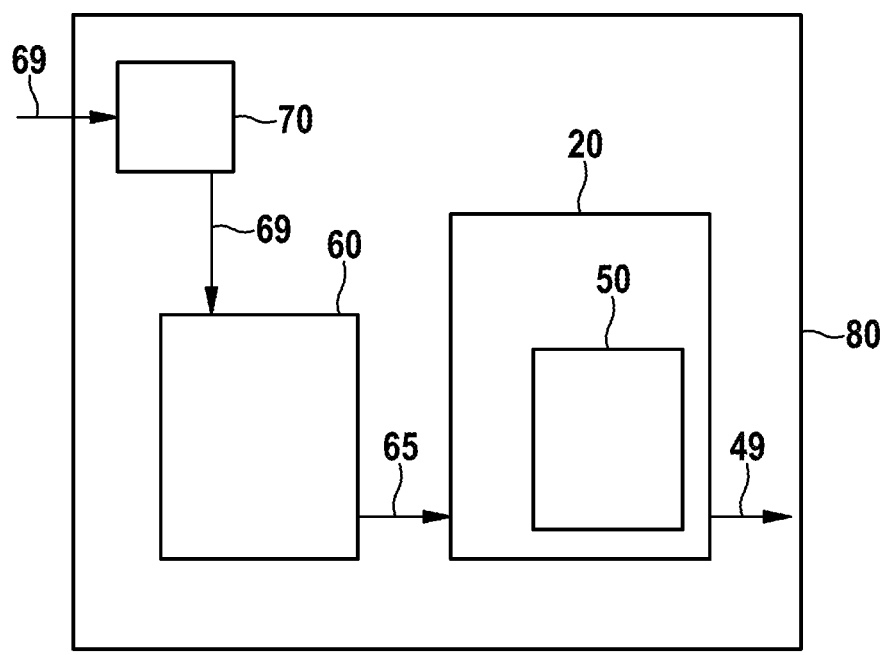
FIG. 1 shows a schematic drawing of an exemplary embodiment of an implantable cardiac device according to the present invention.

FIG. 1 shows a schematic drawing of an exemplary embodiment of an implantable cardiac device 80 according to the present invention. In this exemplary embodiment, the implantable cardiac device 80 is exemplarily realized as a pacemaker, which comprises a sensing unit 70 that is adapted to measure an intrathoracic or intracardiac impedance input stream 69 comprising a patient's respiratory waveforms. In other embodiments of the present invention, the sensing unit 70 of the implantable cardiac devices 80 is adapted to measure an intrathoracic and/or an intracardiac pressure and/or an accelerometry input stream 69 comprising a patient's respiratory waveforms. In this embodiment, the sensing unit 70 is exemplarily realized as an impedance based respiration monitor that is exemplarily connected to a pacemaker lead which is positioned in the right atrium, right ventricle or left ventricle of a patient, depending on the kind of therapy-device the implantable cardiac device 80 is realized as. According to that, the implantable cardiac device 80, for example, can be realized as a pacemaker, defibrillator, cardiac resynchronization device, or as implantable monitoring device. However, other sensing units 70 with other sorts of leads positioned in other regions of a patient's heart or body can be realized within other embodiments of implantable cardiac devices 80 according to the present invention as will be appreciated by one skilled in the art. In this embodiment of the present invention, the impedance based respiration monitor exemplarily comprises an auto-gain auto-offset block which is suited to remove at least a significant part of the DC-offset from the impedance input stream 69 and then maximizes the AC-part, so the remaining time-varying waveform within the undistorted range limits of the signal path (not shown).

The implantable cardiac device 80 further comprises a quantizer-unit 60 adapted to sample the input stream 69 with an initial sampling frequency Fs, providing input samples 65 of the input stream 69. Furthermore, the implantable cardiac device 80 comprises a filter bank 50 which is suited to perform a streaming Wavelet transformation on the input samples 65 on a sample-by-sample basis in real time, using the initial sampling frequency Fs provided by the quantizer-unit 60, wherein the streaming Wavelet transformation is adapted to perform a source separation, extracting and separating the respiratory waveform of the input samples 65, sampled from the input stream 69. In this embodiment of the present invention, the implantable cardiac device 80 is exemplarily adapted to provide the extracted and separated respiratory waveform as an output waveform via a data output 49. Furthermore in this embodiment, the output waveform containing information about a patient's respiratory waveform is exemplarily transmittable to a home monitoring service center. In other embodiments of the present invention, the output waveform provided by the implantable cardiac device 80 may be displayable to a user via a display or be convertible in another way not mentioned above.

In this embodiment of the present invention, the initial sampling frequency Fs of the quantizer-unit 60 is exemplarily adaptable, wherein in this embodiment of the present invention, the adaptation is exemplarily made according to a change in the heart rate and/or a change in the breathing rate of a patient. The initial sampling frequency Fs is the frequency with which the Wavelet transformation is started off with. With a change of the initial sampling frequency Fs provided by the quantizer-unit 60, a selection of frequency sub-bands given within the input samples 65 as input for the filter bank 50 is performed. Through a change in the sampling frequency, the Wavelet transformation is adjusted, regarding the information evaluated since a change in the initial sampling frequency Fs of the quantizer-unit 60 leads to an adjustment of the position of the Nyquist frequency within the frequency band observed. This will be further discussed in the following Figures.

In this embodiment of the present invention, the Wavelet transformation performed by the filter bank 50 is exemplarily a Haar Lifting Wavelet Transformation. However, other embodiments of the present invention can be carried out in which other Wavelet functions are used in order to perform an extraction and separation of a respiration waveform from an input stream 69 in the sense mentioned further above. For example, an implantable cardiac device 80 according to the present invention can be provided using for example a Wavelet of the Daubechies family or any other Wavelet existing within the state of the art. Furthermore, in this embodiment of the present invention, the filter bank 50 of the implantable cardiac device 80 is exemplarily realized within a digital signal processing unit 20. Expressed in other words, in this embodiment of the present invention, the filter bank 50, with all its highpass- and lowpass-subfilters or filter-units used for the performance of the Mallat-tree decomposition within the Wavelet transformation, is digitally realized within a digital signal processing unit 20 which in this embodiment of the present invention is exemplarily realized as a digital signal processor. Moreover, in this embodiment of the present invention, the Wavelet transformation is exemplarily implemented by means of a recursive algorithm that maximizes the code reuse within the digital signal processing unit 20. During the execution of the Wavelet transformation, for every frequency sub-band of an input sample 65 that is wavelet transformed, the same code is used except that it is varied by the order of operation or the unary sign. However, other embodiments of the implantable cardiac device 80 can be carried out in which other processing units are realized and in which the filter bank 50 is not realized as a recursive algorithm or without a maximum code reuse.

Figure 2:
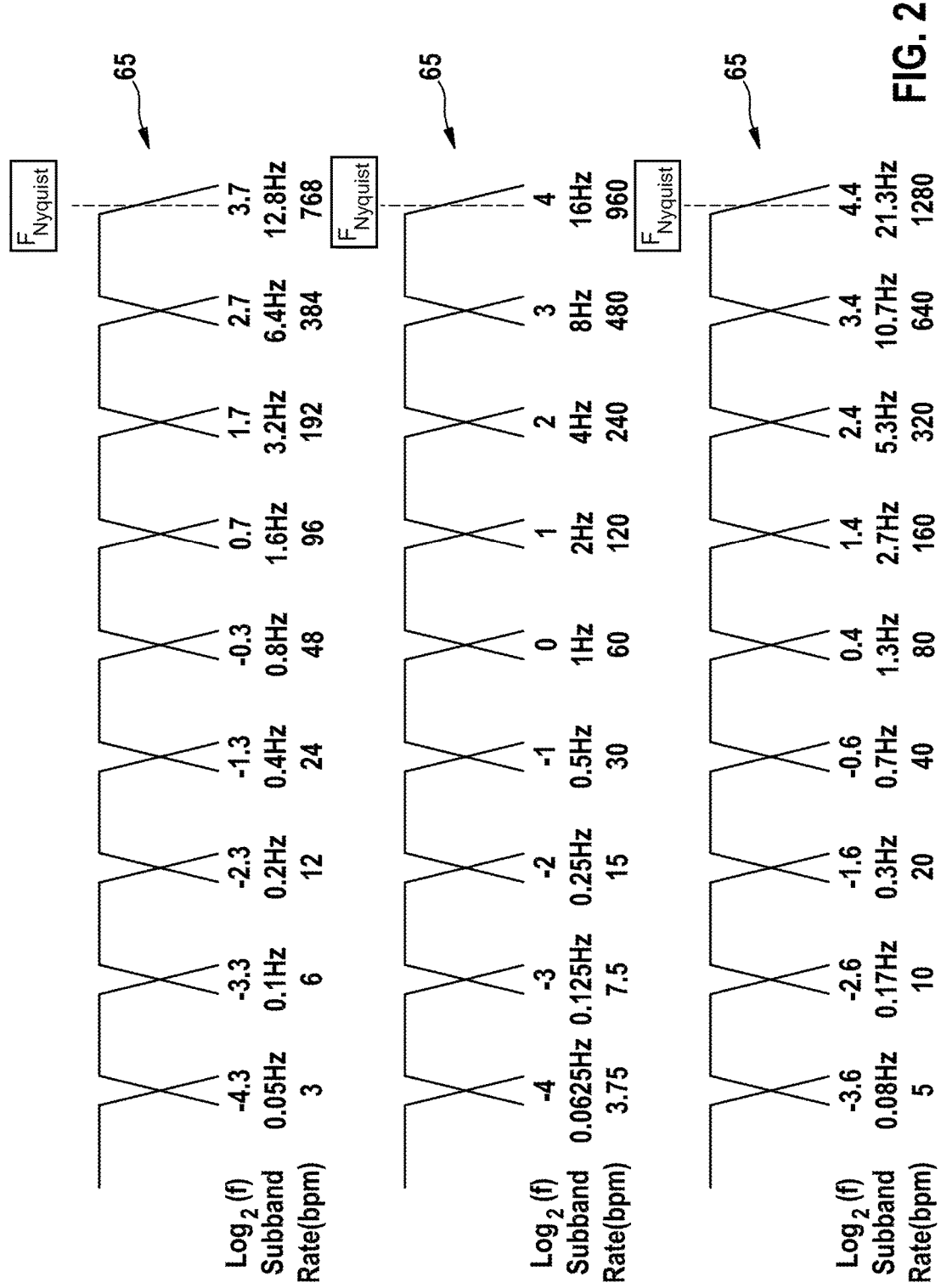
FIG. 2 shows an exemplary frequency diagram of frequency sub-bands containing a patient's respiration waveform at different respiration health states, which are evaluable with an implantable cardiac device according to the present invention.

FIG. 2 shows an exemplary frequency diagram that contains a plurality of frequency sub-bands containing a patient's respiration waveform at different respiration health states, which are evaluable with an implantable cardiac device 80 according to the present invention. Expressed in other words, FIG. 2 shows input samples 65 of a patient's respiratory waveform that have been sampled at different initial sampling frequencies Fs, each adapted in its value for a precise detection of the respective health state. Expressed more precisely, three different input samples 65 are shown in FIG. 2, each containing frequency sub-bands which occur at different respiration health states and which have been sampled with different initial sampling frequencies Fs chosen according to the respective health state analyzed. Furthermore, for each input sample 65 and for each frequency sub-band within the input sample 65, the respective value of the logarithm to the base 2 of the respectively belonging frequency, the respectively belonging frequency sub-band range or length in Hz and the respectively belonging respiratory rate in bpm, is provided. Additionally, for each input sample 65, the Nyquist frequency "FNyquist" is marked which depends on the respective initial sampling frequency Fs and which divides the usable frequency band from the unusable frequency band, in which, for example, aliasing becomes an issue. The uppermost diagram of the three diagrams of FIG. 2 shows an input sample 65 containing frequency sub-bands of a patient suffering from Apnea. The lowermost diagram of the three diagrams of FIG. 2 shows an input sample 65 containing frequency sub-bands of a patient suffering from Tachypnea, wherein the intermediate diagram of the three diagrams of FIG. 2 shows an input sample 65 containing frequency sub-bands of a patient showing a "normal" respiration rate.

In FIG. 2, for all three diagrams, it can be seen that the frequency sub-bands are stretched and squeezed depending on the change of the initial sampling frequency Fs provided by the quantizer-unit 60. The frequency sub-bands are stretched accordingly with an increase of the initial sampling frequency Fs of the quantizer-unit 60. Given, for example, the input sample 65 shown in the middle diagram, at a sample rate between 3.75 bpm and 7.5 bpm, a frequency sub-band has a range of 0.0625 Hz to 0.125 Hz. In contrast, the frequency sub-band range sampled for a physiologic event rate between 480 bpm and 960 bpm is equal to 4 Hz to 8 Hz, having a frequency sub-band range that is 64 times larger than the range of the frequency sub-band sampled for a respiratory rate between 3.75 bpm and 7.5 bpm. As already described, through an adjustment of the initial sampling frequency Fs of the quantizer-unit 60, it is possible to select and to maximally discriminate a single or a plurality of frequency sub-bands from all three diagrams shown in FIG. 2. Such a change in the initial sampling frequency Fs provided by the quantizer-unit 60 can be performed, without that a concomitant change to the filter bank 50 or its coefficients to keep it working properly is needed.

Figure 3:
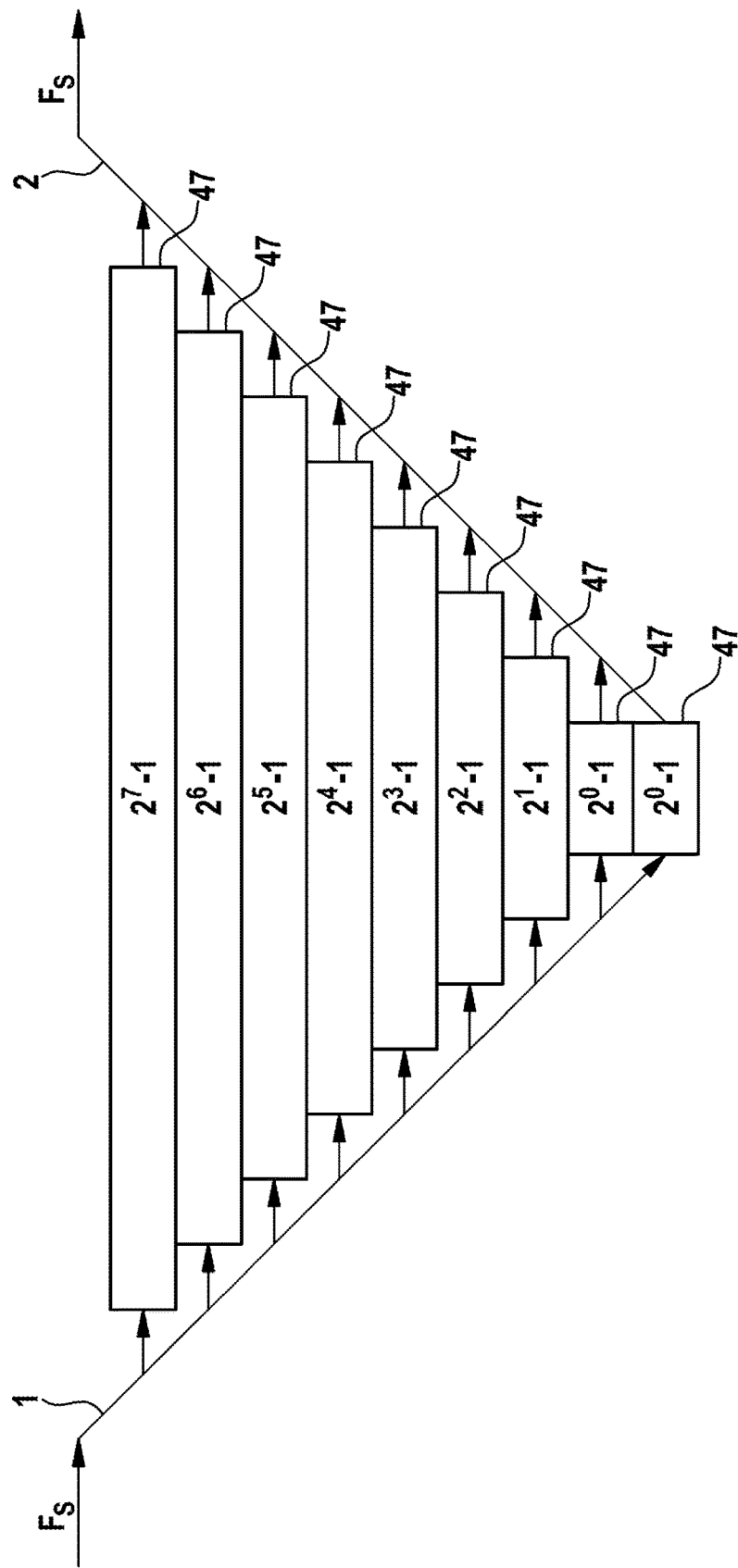
FIG. 3 shows a schematic illustration of an execution of an exemplary Wavelet transformation performed by an exemplary embodiment of an implantable cardiac device according to the present invention.

FIG. 3 shows a schematic illustration of an execution of an exemplary Wavelet transformation performed by an exemplary embodiment of an implantable cardiac device 80 according to the present invention. Expressed more precisely, FIG. 3 schematically shows how an exemplary Wavelet transformation is performed on an exemplary input sample 65 by the filter bank 50, starting on the left end side and ending on the right end side of FIG. 3. In this exemplary embodiment of the implantable cardiac device 80, the filter bank 50 is adapted to perform a streaming Wavelet transformation comprising a forward transformation, shown at 1, and a backward transformation, shown at 2, represented by the arrows shown in the diagram. The Wavelet transformation is executed from the left to the right on each input sample 65. Expressed in other words, in this embodiment of the present invention, during the forward transformation 1, the Wavelet transformation is applicable on each input sample 65 provided by the quantizer-unit 60 generating output data 47 on "n" different sampling levels, wherein the output data 47 generated on the sampling levels is queued and the sampling frequency used to sample an input sample 65 on a sample level "t" is equal to 2 times the sampling frequency of the sampling level t−1, wherein "n" and "t" are elements of $N^+$. $N^+$ denotes natural numbers greater than zero. So the output data 47 generated within the forward transformation is retained in a central queue structure, where the length of the queue $2^{(n-t)}-1$.

In the diagram of FIG. 3, which shows an inverted pyramid, each bar represents output data 47 generated within the forward transformation 1 of the Wavelet transformation of a single frequency sub-band of an input sample 65. Expressed in other words, each bar of the diagram shown in FIG. 3 is relatable to one frequency sub-band, for example, as they are shown in FIG. 2. The length of the bar represents the range of the frequency sub-band represented by the respective output data 47. The highest and longest bar in the diagram of FIG. 3 therefore shows the output data 47 corresponding to a frequency sub-band that has been sampled with the highest sampling frequency of the showed cycle of operation of the Wavelet transformation, so the initial sampling frequency Fs, which in this example exemplarily is near to a sample rate of 128 Hz. This frequency sub-band of the input sample 65 was transformed on the highest sampling level, thus the n-th sampling level of the Wavelet transformation in that cycle of operation, wherein in this example "n" is equal to 9. According to the Mallat algorithm performed by the filter bank 50, the next smaller bar in the diagram of FIG. 3, n−1, shows output data 47 that represents a frequency sub-band of the input sample 65 that was sampled with about half the initial sampling frequency Fs. Since the sampling frequency is reduced, the bar or the represented frequency sub-band is reduced in its range, which is shown as a shorter sized bar in the diagram of FIG. 3. Furthermore, in FIG. 3, the sampling frequencies used for the generation of the output data 47 for each frequency sub-band is given in the middle of each bar. For the next sampling level, the sampling frequency is halved again and so forth, until the lowest level of the forward transformation is reached, wherein the output data 47 generated on a sampling level "t" is used in order to compute the output data on next lower sampling level t−1.

In this embodiment of the present invention, the Wavelet transform provides for zero wait $2^0-1=0$ at its two lowest levels. The bottom two bars of FIG. 3 therefore show the zero-wait $2^0-1=0$. That is, those queues have zero length. Upon production of these values, they can be used immediately without wait by the backward transformation 2 or the reconstruction arm of the Wavelet transformation.

However, this kind of performance of the Wavelet transformation is only optional and can be different to the ones performed in other embodiments of the present invention. Also other embodiments of the present invention can be carried out in which the length of the queue may be governed by another relationship, especially when a different kind of Wavelet transformation than the one described herein is used. Within the backward transformation 2 of the Wavelet transformation, the output data 47 on the "n" different sampling levels is reassembled, wherein from sampling level to sampling level, an upsampling of the output data 47 generated within the forward transformation 1, is performed. In the example shown in FIG. 3, within the backward transformation 2, an upsampling is performed until the initial sampling frequency Fs is reached again.

Figure 4:
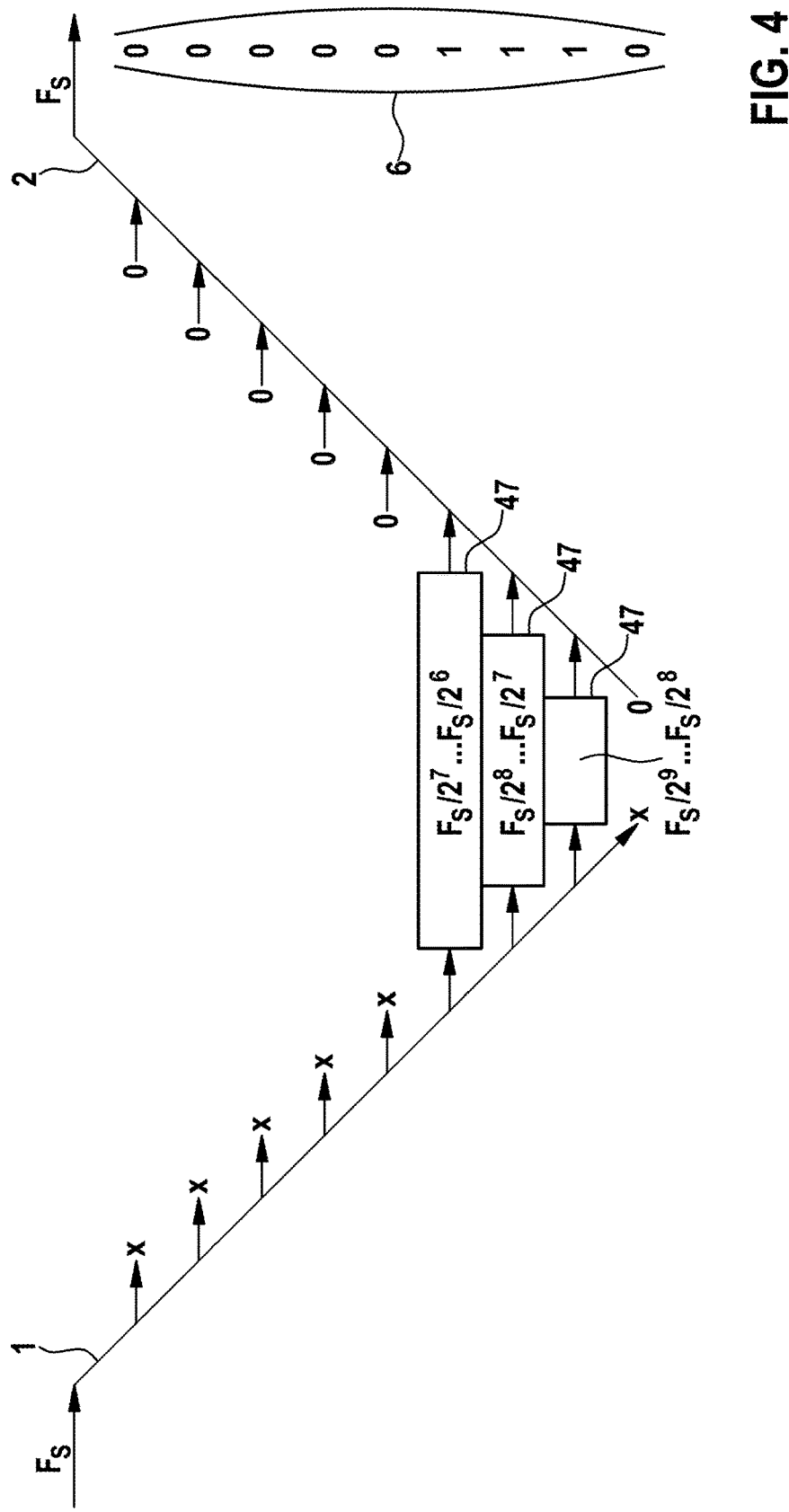
FIG. 4 shows a schematic illustration of an execution of another exemplary Wavelet transformation performed by an exemplary embodiment of an implantable cardiac device that is capable of discarding output data from the queue according to the present invention.

FIG. 4 shows a schematic illustration of an execution of another exemplary Wavelet transformation performed by an exemplary embodiment of an implantable cardiac device 80 that is capable of discarding output data 47 from the queue according to the present invention. FIG. 4 basically shows the diagram of FIG. 3 with a few differences that will be addressed in the following. FIG. 4 again shows a Wavelet transformation with a forward transformation 1 and a backwards transformation 2 performable by an implantable cardiac device 80 according to the present invention. In this embodiment of an implantable cardiac device 80 according to the present invention, the filter bank 50 of the implantable cardiac device 80 is adapted to discard or exclude output data 47 generated on one or more than one sampling levels, after the respectively suspended output data 47 has been used to compute the output data 47 for the next lower sampling level. Expressed in other words, in this embodiment of the implantable cardiac device 80, output data 47 generated on a certain sampling level, that represents a certain frequency sub-band, can be selectively discarded or kept as output data 47 throughout the performance of the Wavelet transformation. So in this embodiment of the present invention, transformed frequency sub-bands of an input sample 65, that have been transformed on a certain sampling level "t" and that are not needed for a reconstruction of a respiratory waveform, are discardable and excludable from the queuing process during the performance of the Wavelet transformation, after they have been used for the calculation of the output data 47 of the sampling level t−1. So a sub-band stream that will not be used for the reconstruction during the backward transformation 2 of the Wavelet transformation is simply not queued after its value has been used to generate a lower frequency sub-band value as output data 47 the lower frequency sub-band is represented by.

Furthermore, in this embodiment of the present invention, the information, whether certain output data 47 is needed for the reconstruction of a respiratory waveform, or discarded from the Wavelet transformation, is stored as a Boolean value in an indication vector 6. So the indicator for the decision to retain or to discard one or more transformed frequency sub-bands is encoded as a vector 6 of Boolean types (1 or 0). In FIG. 4, that output data 47 that is not queued is indicated by an "X" on the forward transformation 1 side of the Wavelet transformation and by a "0" on the backward transformation 2 side of the Wavelet transformation, while "0" is also the entry within the indication vector 6 that is set in the case in which output data 47 is discarded. Output data 47 that is kept and queued is marked with a "1" at the respective slot of the indication vector 6. So for every (transformed) frequency sub-band, there is a respective slot within the indication vector 6, which is also shown in FIG. 4. The values of the indication vector 6 serve doubly to gate the input on the reconstruction side, so the backward transformation 2 side of the Wavelet transformation as shown in the diagram of FIG. 4.

In the example shown in FIG. 4, only the output data 47 representing three frequency sub-bands is kept and queued. Referring back to the middle diagram of FIG. 2, the three frequency sub-bands retained represent a group of contiguous frequency sub-bands spanning frequencies from 0.0625 Hz to 0.5 Hz in order to extract the respiration waveform in the range of 3.75 bpm to 30 bpm, given the initial sampling frequency Fs, with which the input stream 69 is sampled, is equal to 32 Hz.

Figure 5:
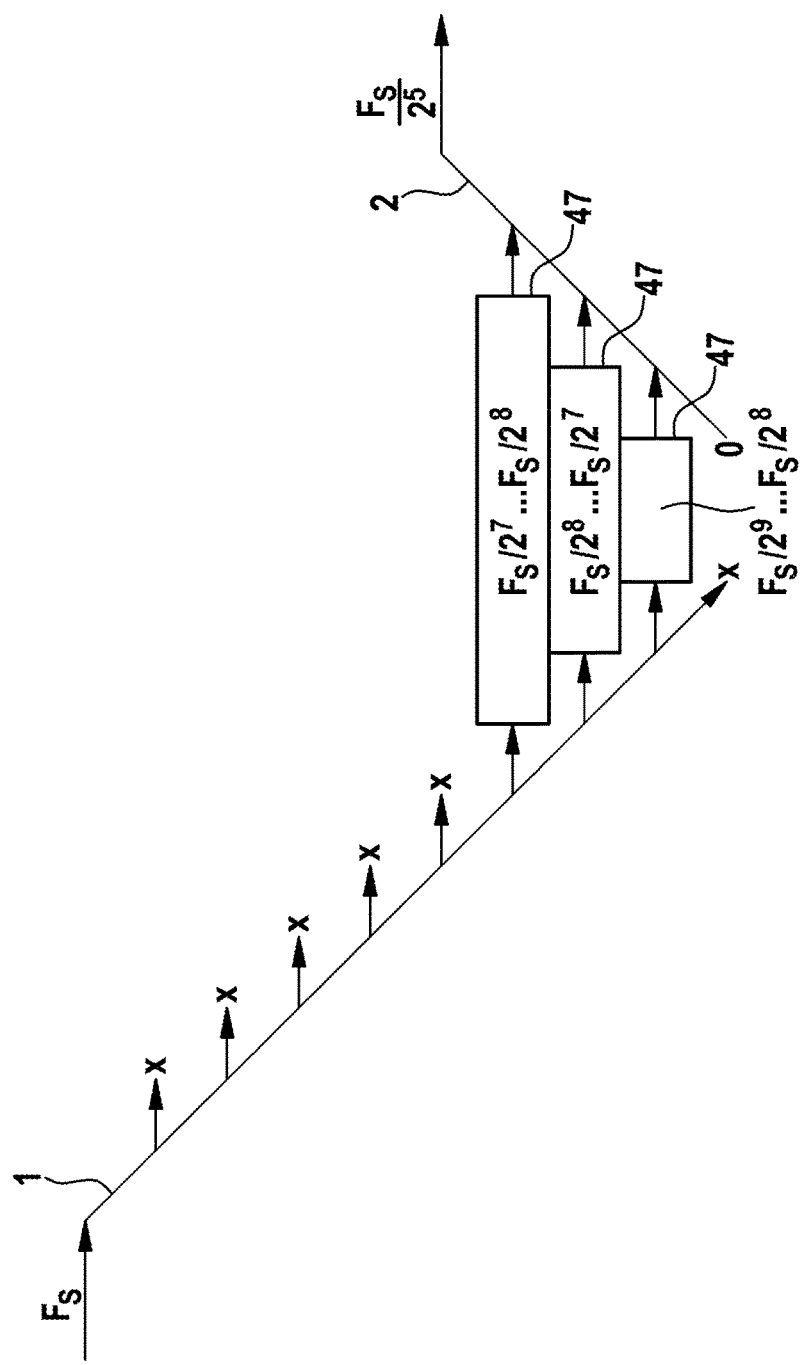
FIG. 5 shows a schematic illustration of an execution of another exemplary Wavelet transformation performed by an exemplary embodiment of an implantable cardiac device that is capable of evaluating output data on a sampling level that is lower than the sampling level of the initial sampling frequency according to the present invention.

FIG. 5 shows a schematic illustration of an execution of another exemplary Wavelet transformation performed by an exemplary embodiment of an implantable cardiac device 80 that is capable of evaluating output data 47 on a sampling level that is lower than the sampling level of the initial sampling frequency Fs according to the present invention. The exemplary Wavelet transformation illustrated in FIG. 5 can be seen as a further development of the Wavelet transformation illustrated in FIG. 4. However, a filter bank 50 of an implantable cardiac device 80 according to the present invention can also be adapted to perform the Wavelet transformation presented in FIG. 5 without being adapted to perform the Wavelet transformation presented in FIG. 4. In this embodiment of the present invention, the filter bank 50 is adapted to perform a Wavelet transformation, in which during the backward transformation 2, an upsampling is also only performable up to the highest sampling level on which output data 47 is retained, wherein the output data 47 transformed on that highest sampling level is evaluable with the sampling frequency of that highest sampling level. Expressed in other words, in this embodiment of the present invention, during the backward transformation 2 of the Wavelet transformation, an upsampling does not has to be performed back up to the sampling frequency the forward transformation 1 has begun with.

In the example shown in FIG. 5, only the output data 47 representing the three frequency sub-bands already described in FIG. 4 is retained and queued. So in this example, again, only the group of contiguous frequency sub-bands spanning frequencies from 0.0625 Hz to 0.5 Hz, as shown in FIG. 2, is kept, while the output data 47 corresponding to the remaining frequency sub-bands is discarded. The difference between the Wavelet transformation illustrated in FIG. 5 to the one illustrated in FIG. 4 is, that during the backward transformation 2, an upsampling is only performed up to the highest sampling level on which output data 47 was kept. In this example, this sampling level is characterized by a sampling frequency that is in between $Fs/2^7 \ldots Fs/2^6$ Hz. The output data 47 generated on that sampling level is not upsampled back up to the initial sampling frequency Fs. Instead, it is evaluated with a sampling frequency which is equal to $Fs/2^5$ Hz. So once the highest retained frequency sub-band or the output data 47 representing it is restored to the output signal, further computation and memory use can be eliminated by posting the output signal at the lower sample rate. If, as in FIG. 4, the initial sampling frequency Fs is equal to 32 Hz, the lower sample rate or sampling frequency is equal to 1 Hz.

Figure 6:
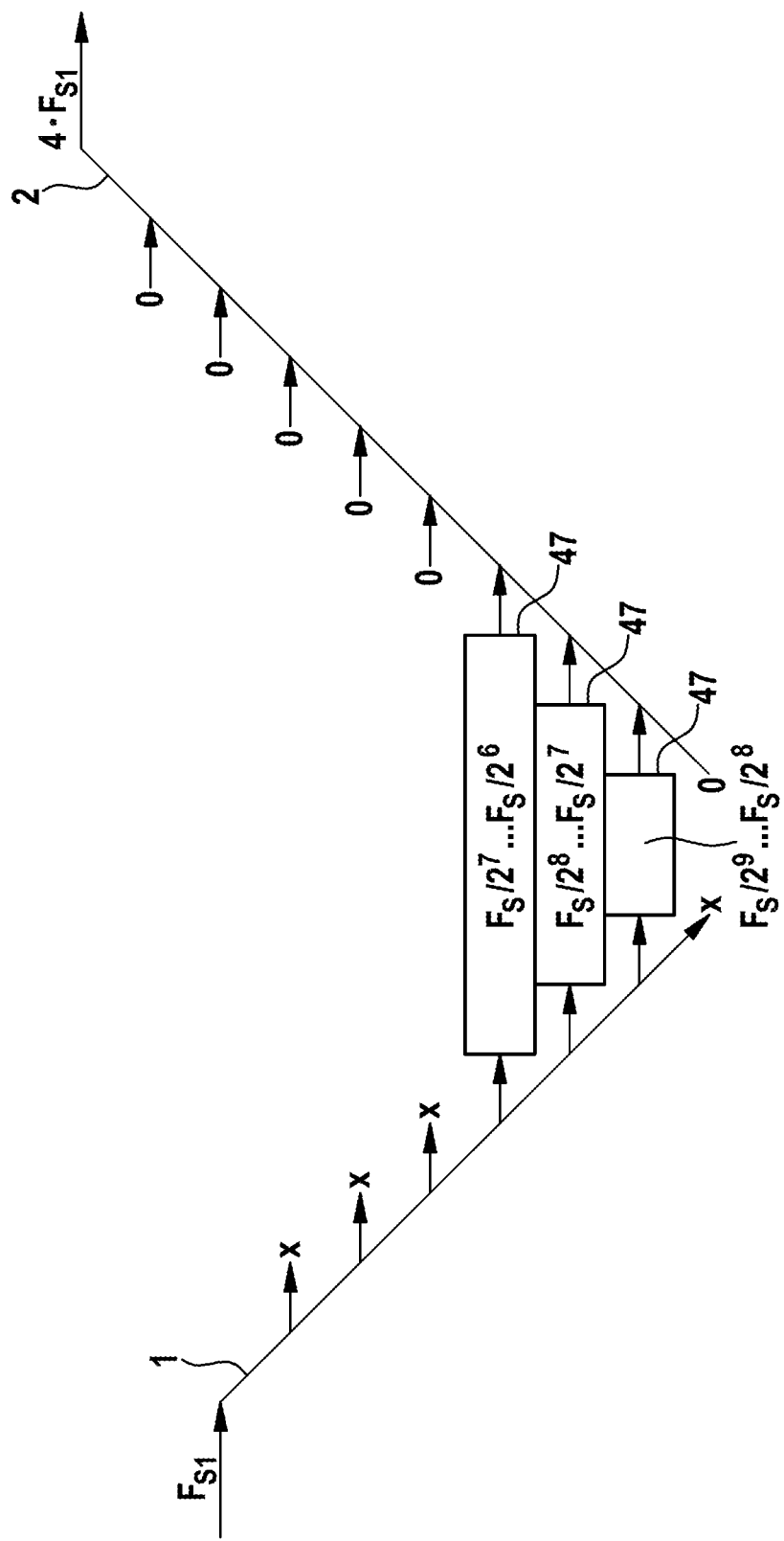
FIG. 6 shows a schematic illustration of an execution of another exemplary Wavelet transformation performed by an exemplary embodiment of an implantable cardiac device that is capable of evaluating output data on a sampling level that is higher than the sampling level of the initial sampling frequency according to the present invention.

FIG. 6 shows a schematic illustration of an execution of another exemplary Wavelet transformation performed by an exemplary embodiment of an implantable cardiac device 80 that is capable of evaluating output data 47 on a sampling level that is higher than the sampling level of the initial sampling frequency Fs according to the present invention. In this embodiment of the implantable cardiac device 80 according to the present invention, the filter bank 50 is adapted to, during the backward transformation 2, perform an upsampling of the output data 47 of a transformed input sample 65 beyond the sampling level of the initial sampling frequency Fs used within the forward transformation 1, and to evaluate the output data 47 on that sampling level. In this embodiment of the present invention, the implantable cardiac device 80 is adapted to provide at least two different input samples 65 of the same or a different input stream 69 at different sampling frequencies. Since in some cases, the output data 47 resulting from a forward transformation 1 of both these input samples 65 needs to be evaluated on the same sampling level or with the same sampling frequency, the output data 47 belonging to the first input sample 65 sampled with a lower sampling frequency needs to be upsampled to the higher sampling frequency of the output data 47 belonging to the second input sample 65. This is shown in the diagram of FIG. 6 where again, the out-put data 47 of the three frequency sub-bands from FIGS. 4 and 5 is shown as a transformed first input sample 65. In this example, the initial sampling frequency Fs1 that was used to generate the output data 47 belonging to the first input sample (shown in FIG. 6) within the forward transformation 1 was Fs1=8 Hz. The output data 47 belonging to the second input sample 65 (not shown in FIG. 6) was generated with an initial sampling frequency Fs2 with Fs2=32 Hz. In this example, during the backward transformation 2 of the Wavelet transformation, the output data 47 representing the three described frequency sub-bands of the first input sample 65 is upsampled an additional two levels in order to reach conformity with the transformed second input sample 65. These two additional sampling levels mean an upsampling of the output data 47 of the forward transformation to 4*Fs1=32 Hz, which is equal to the initial sampling frequency Fs2 of the transformed second input sample 65. This upsampling beyond the initial sampling frequency Fs1 of the first input sample 65 is performable without concomitant detrimental effects on the frequency content, such as, for example, aliasing, since the missing frequency sub-bands are treated as discarded, as explained in the description of FIG. 4. The result is a first output waveform derived from the first input sample 65, which is directly comparable with a second output waveform derived from the second input sample 65 and sampled with an initial sampling frequency Fs2=32 Hz.

Figure 7:
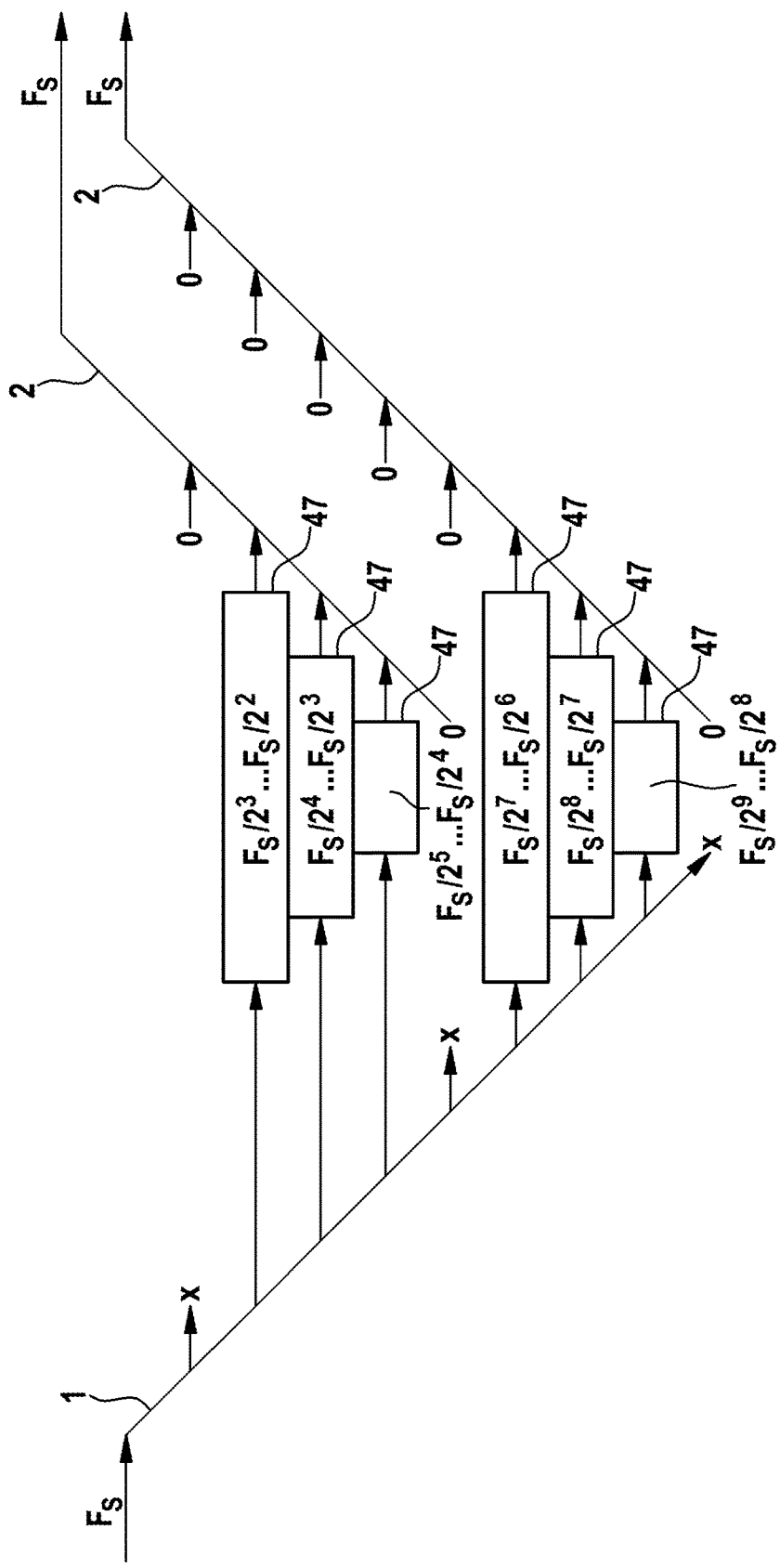
FIG. 7 shows a schematic illustration of an execution of another exemplary Wavelet transformation performed by an exemplary embodiment of an implantable cardiac device that is capable of evaluating output data of at least two different transformed input samples of the same input stream simultaneously according to the present invention.

FIG. 7 shows a schematic illustration of an execution of another exemplary Wavelet transformation performed by an exemplary embodiment of an implantable cardiac device 80 that is capable of evaluating output data 47 of at least two different transformed input samples 65 of the same input stream 69 simultaneously according to the present invention. In this embodiment of the present invention, the filter bank 50 of the implantable cardiac device 80 is adapted to perform a Wavelet transformation on at least two different input samples 65 of the same input stream 6, wherein during the backward transformation 2, the output date 47 belonging to the input samples 65 is upsampleable to the same sampling frequency and evaluable simultaneously with the sampling frequency they have been upsampled to.

In FIG. 7, two input samples 65 from the same input stream 69 are transformed within the forward transformation 1 of the same operation cycle of the Wavelet transformation, generating output data 47 that for each input sample 65 represents three frequency sub-bands which are different to one another. The first input sample 65 shown in the diagram of FIG. 7 is transformed to output data 47 sampled on sampling levels with sampling frequencies that vary from $Fs/2^2$ to $Fs/2^5$, while the second input sample 65 is transformed to output data 47 sampled on sampling levels with sampling frequencies that vary from $Fs/2^6$ to $Fs/2^9$ within the forward transformation 1. Since both input samples 65 are derived from the same input stream 69, the same initial sampling frequency Fs has been used for the transformation of both input samples 65. During the backward transformation 2 of the Wavelet transformation, the output data 47 resulting from the forward transformation 1 of both input samples 47 is upsampled to the same sampling level, in this case to the initial sampling frequency Fs, and is evaluated on this sampling level.

Expressed in other words, in this embodiment of the present invention, the filter bank 50 is capable of simultaneously extracting two or more distinct physiological signals, the first and second input samples 47, containing different frequency sub-bands of the same input stream 69 while maintaining their concurrency. Furthermore, in this embodiment of the present invention, the filter bank 50 is additionally adapted to conjoin two or more input samples 65 from different input streams 69 in the manner described above.

Figure 8:
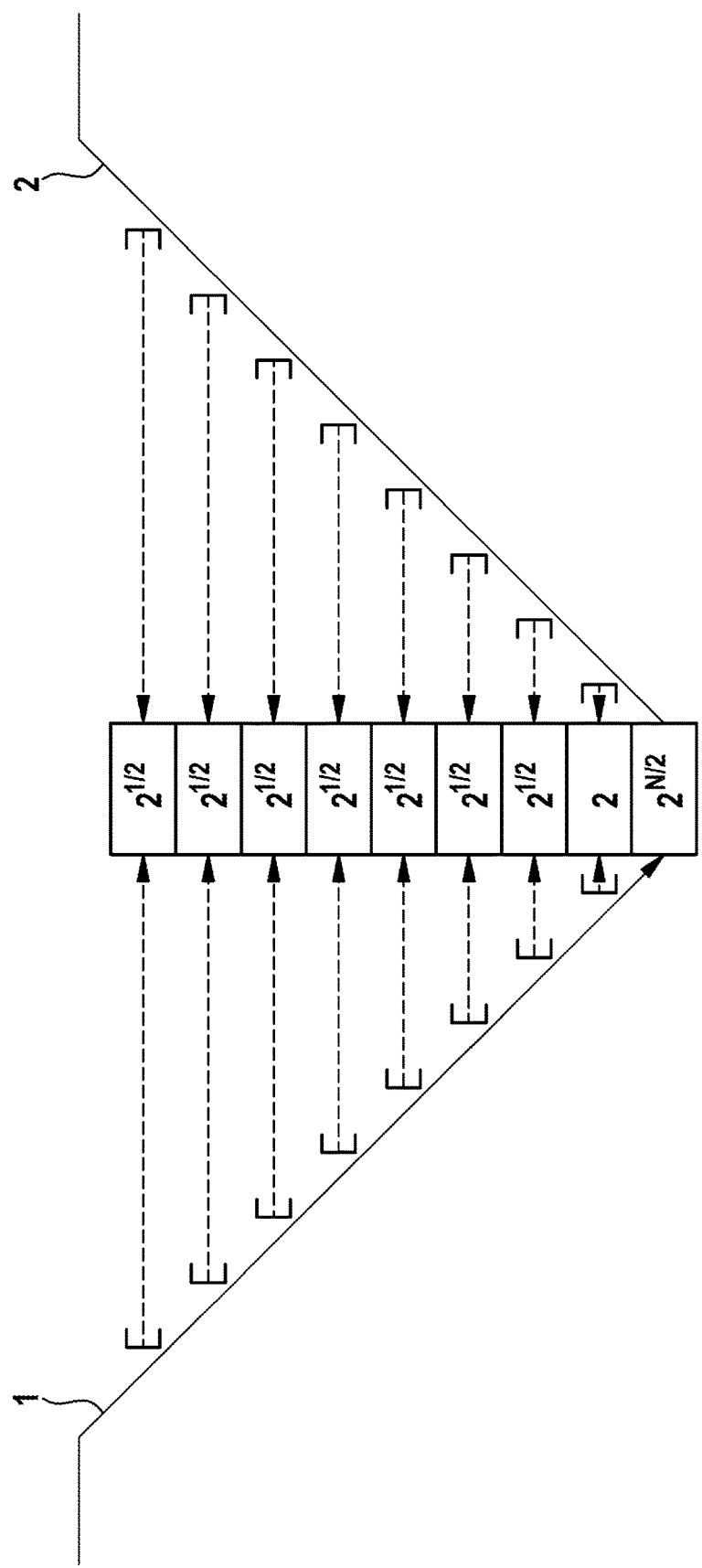
FIG. 8 shows a schematic illustration of the computation of characteristic parameters for an exemplary input sample of an input stream performable by an exemplary embodiment of an implantable cardiac device according to the present invention.

FIG. 8 shows a schematic illustration of the computation of characteristic parameters for an exemplary input sample 65 of an input stream 69 performable by an exemplary embodiment of an implantable cardiac device 80 according to the present invention. In this embodiment of the present invention, the implantable cardiac device 80 is adapted to compute a parameter and a probabilistic function for all the input samples 65 and for all the frequency sub-bands contained within these input samples 65 which are generated from input streams 69 captured by the implantable cardiac device 80. In this embodiment of the present invention, for every frequency sub-band given within an input sample 65, a parameter is computed and stored within a vector that represents a "slice" through the output data 47 which has been generated within the forward transformation 1 of the respective input sample 65. Furthermore, in the example shown in FIG. 8, the parameters stored in the vector exemplarily represent the scale values which have been used within the performance of the Wavelet transformation in order to transform a respective frequency sub-band. In such an embodiment of the present invention, each frequency sub-band can properly be quantified using the scale values stored in the vector. In FIG. 8, for each frequency sub-band, the respective scale value is shown in the center of the diagram.

However, other embodiments of implantable cardiac devices 80 according to the present invention can be carried out in which the parameters stored within the vector describe other properties of the frequency sub-bands or of an input sample 65, as will be appreciated by one skilled in the art. For example, an implantable cardiac device 80 can be realized which is adapted to compute and store parameters which represent the respective average energy of a frequency sub-band or another informative property of a frequency sub-band or input sample 65. In an embodiment of the present invention, in which the average energy of the frequency sub-bands is computed and stored in a vector, the average energy among restored and queued frequency sub-bands across the vector can be corresponding to the respiration rate of the patient in whom the implantable cardiac device 80 is implanted. Furthermore, in other embodiments of the present invention, a scaling value is not applied to each value on a sample basis, but to the final value of the vector, in order to minimize operations. In such an embodiment, if the scaling factor is the same, its application can be deferred until individual values are aggregated. Then, the scaling factor can be applied to the aggregate. The advantage of this is that the feature extraction and separation can proceed without the need to properly scale the values and the final output will still be quantitatively correct. Therefore, in such an embodiment, the application of the scaling factor to the aggregate of the individual values can serve as a further modification to reduce the computational load.

Furthermore, in this embodiment of the present invention, the implantable cardiac device 80 is adapted to compute a probabilistic function providing information about a statistical distribution of an input sample 65. In other embodiments of the present invention, the implantable cardiac device 80 is adapted to compute a probabilistic function providing information about a statistical distribution related to an input sample 65. Moreover, in this embodiment of the present invention, the implantable cardiac device 80 is adapted to determine whether a computed and stored probabilistic function is capable of accurately indicating a suitable signal quality for a measurement of respiration or a noisy state. Furthermore, the implantable cardiac device 80 of this embodiment is adapted to perform subsequent observations of the computed vectors described and probabilistic functions and to aggregate the same in order to generate probability models for prediction or the classification of changes to the input stream 69. In this embodiment of the present invention, these changes can indicate a declining or improving quality of the input stream 69 which, in this embodiment of the present invention, exemplarily can lead to a suspension or a resumption of the activity of the sensing unit 70, in this embodiment the respiration monitor, or it can indicate a change in the health state of the patient.

In some embodiments of the implantable cardiac device 80, the performance of the Wavelet transformation and the parameter extraction, as described above, is operated for a set, predefined time. However, in this embodiment of the present invention, the transformation procedure, namely, the execution of the Wavelet transformation and the parameter extraction as described above, is controlled by a quality figure, wherein the observation period, namely, the time in which the Wavelet transformation and the parameter extraction is executed as described above, is linked to a number of physiological events which are sufficient to yield a value meeting a reliability or confidence threshold. Expressed in other words, in this exemplary embodiment of the present invention, a Wavelet transformation as described further above, performed in order to extract a patient's respiratory waveform, just as the computation of parameters and probabilistic functions to provide information, is only initiated if a number of physiological events which are sufficient to yield a value meet a reliability or confidence threshold. Furthermore, the implantable cardiac device 80 of this embodiment is adapted to sum up the amplitudes of the frequency sub-bands over the observation period in order to generate a metric which is directly related to a patient's tidal volume in the time domain.

In some embodiments of the present invention, a change in the health state of the patient the implantable cardiac device 80 is implanted in can result in an adjustment of the operation of the implantable cardiac device 80, especially in a change of the initial sampling frequency Fs. Furthermore, in embodiments of the present invention, such a change in the health state of the patient leads to a change in the way the information is communicated to a home monitoring service center. Moreover, an embodiment of the present invention can be carried out, in which probabilistic functions are computed which describe the frequency distribution over time. For example, in such embodiments, a further accelerometer, position or temperature sensor can be provided within the implantable cardiac device 80, which is used in conjunction with the probabilistic functions describing the frequency distribution over time in order to make inferences about autonomic tone response to cold stress of the patient, wherein cold stress is a metric of the cardiac health state.

Furthermore, in this embodiment of the present invention, the implantable cardiac device 80 is adapted to measure parameters from the output waveform, or the outputted real-time respiration waveform of the implantable cardiac device 80. In this embodiment of the present invention, the implantable cardiac device 80 is exemplarily adapted to measure, among others, the breathing rate (RR) as the cycle time of a repeating fiducial point in the breath cycle. These points may be positive-going zero-crossing, negative-going zero-crossing, peak-to-peak, trough-to-trough and/or same-going inflection points near zero-crossing. Furthermore, in this embodiment of the present invention, the implantable cardiac device 80 is exemplarily adapted to measure the tidal volume (TV) as the trough-to-peak, peak-to-trough amplitudes in Ohms and the tidal volume (TV) adjusted as the tidal volume (TV) modified to compensate for breath-to-breath variations in end-expiratory volume which appear to leave the end of breath at a different offset from the beginning of the same breath. For example, if the breath start is assumed as reference and the trailing offset is subtracted from the area under the breath feature, which represents the instantaneous minute ventilation (MV), the implantable cardiac device 80 is suited to calculate the adjusted tidal volume (TVADJUST) as the quotient of the instantaneous minute ventilation (MVINSTANT) and the instantaneous breathing rate (RRINSTANT), so TVADJUST=MVINSTANT/RRINSTANT. Furthermore, in this embodiment of the present invention, the implantable cardiac device 80 is exemplarily adapted to measure the Inspiratory:Expiratory (I:E) ratio as the time of trough-to-peak versus the time of peak-to-trough and the Inspiratory:Expiratory (I:E) ratio adjusted as the I:E times adjusted by inspiratory or expiratory hold times.

In this embodiment of the present invention, when parameters can be calculated by more than one means of the implantable cardiac device 80, the multiple means can be used in conjunction to provide a parameter with higher statistical confidence. In this embodiment of the present invention, the implantable cardiac device 80 is further adapted to identify inspiratory holds and breath pauses, such as apneic periods between breaths, and adapted to correct its calculation of dependent morphological breath parameters, such as the I:E ratio, likewise. Moreover, in this embodiment of the present invention, the implantable cardiac device 80 is adapted to use morphological breath parameters to screen breath cycles as modified for example by speaking, coughing, and sighing.

So, in this embodiment of the present invention, the real-time respiration waveform is analyzed to produce parameters indicating for example the respiration rate of a patient, the tidal volume of a patient, the I:E ratio of a patient and the minute ventilation of a patient. Further parameters of the patient's individual breath cycles are evaluated against limits based on the physiological principles behind them, such as a maximum I:E ratio of 1:1 for spontaneous respiration, in order to adjust the calculated parameters and to reject the interference caused for example by body movement or the position of the patient.

It has to be mentioned, that implantable cardiac devices 80 according to the present invention can be carried out which combine all the features mentioned above and which are especially capable of performing all the Wavelet transformations described herein, in combination and simultaneously. Expressed in other words, implantable cardiac devices 80 according to the present invention can be carried out, which are adapted to perform all Wavelet transformations described in this document, as will be appreciated by one skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable cardiac device, comprising:
   a device housing;
   a sensor adapted to measure a physiological signal input stream, comprising a patient's respiratory waveforms;
   a quantizer adapted to sample the measured physiological signal input stream with an initial sampling frequency Fs, providing input samples of the measured physiological signal input stream; and
   a filter suited to perform a streaming Wavelet transformation on the input samples on a sample-by-sample basis, using the initial sampling frequency Fs provided by the quantizer, wherein the streaming Wavelet transformation is adapted to perform a source separation, extracting, and separating the patient's respiratory waveforms of the measured physiological signal input stream, and providing the extracted and separated respiratory waveform as an output waveform via a data output,
   wherein the Wavelet transformation is performed in real time without matrix processing,
   wherein the initial sampling frequency Fs of the quantizer is adaptable,
   wherein the initial sampling frequency Fs of the quantizer is adapted according to a change in a heart rate and/or a change in a breathing rate of the patient,
   wherein the sensor, the quantizer and the filter are provided within the device housing, and
   wherein the filter is adapted to perform the streaming Wavelet transformation comprising a forward transformation and a backward transformation, wherein during the forward transformation, the streaming Wavelet transformation is performed on each input sample provided by the quantizer generating output data on n different sampling levels, wherein the output data generated on the n different sampling levels is queued and a sampling frequency used to sample an input sample on a sampling level t is equal to 2 times a sampling frequency of a sampling level t−1, wherein n and t are elements of $N^+$.

2. The implantable cardiac device of claim 1, wherein the Wavelet transformation performed by the filter is a Haar Lifting Wavelet Transformation.

3. The implantable cardiac device of claim 1, wherein the filter is provided within a digital signal processing unit.

4. The implantable cardiac device of claim 3, wherein the Wavelet transformation is performed using a recursive algorithm.

5. The implantable cardiac device of claim 1, wherein output data of the sampling level t, that is not needed for a reconstruction of the patient's respiratory waveform, is discarded and excluded from a queuing process during performance of the streaming Wavelet transformation, after it has been used for calculation of the output data of the sampling level t−1.

6. The implantable cardiac device of claim 5, wherein information, whether output data is needed for reconstruction of the patient's respiratory waveform, or discarded from the streaming Wavelet transformation, is stored as a Boolean value in an indication vector.

7. The implantable cardiac device of claim 5, wherein during the backward transformation, an upsampling is performed up to a highest sampling level on which output data is retained, wherein the output data of the input samples transformed on the highest sampling level is evaluated with the sampling frequency of the highest sampling level.

8. The implantable cardiac device of claim 1, wherein during the backward transformation, an upsampling of the output data generated during the forward transformation is performed beyond a sampling level of the initial sampling frequency Fs used within the forward transformation and evaluated on the sampling level.

9. The implantable cardiac device of claim 1, wherein within the backward transformation, the output data of at least two different transformed input samples of a same input stream is upsampled to a same sampling frequency and evaluated simultaneously with the sampling frequency they have been upsampled to.

10. The implantable cardiac device of claim 1, wherein a parameter and/or a probabilistic function is computed for at least one input sample, wherein the computed parameter or the computed probabilistic function provides information about at least one of a predefined characteristic of the at least one input sample, statistical distribution of the at least one input sample and a statistical distribution related to the at least one input sample.

11. The implantable cardiac device of claim 10, wherein the computed parameter and/or the computed probabilistic function is stored in a vector.

12. The implantable cardiac device of claim 10, wherein the computed parameter represents an average energy of a respective input sample or a scale value used during the streaming Wavelet transformation of the respective input sample.

13. The implantable cardiac device of claim 1, wherein the physiological signal input stream is one of a intrathoracic or intracardiac impedance, a pressure, or a accelerometry signal.

* * * * *